United States Patent
Lim et al.

[11] Patent Number: 5,927,956
[45] Date of Patent: Jul. 27, 1999

[54] PERISTALTIC PUMP TUBING SYSTEM WITH LATCHING CASSETTE

[75] Inventors: Joepert R. Lim, Palm Harbor; Brian J. Fox, St. Petersburg, both of Fla.

[73] Assignee: Linvatec Corporation, Largo, Fla.

[21] Appl. No.: 09/144,730

[22] Filed: Sep. 1, 1998

[51] Int. Cl.⁶ ................................................ F04B 43/12
[52] U.S. Cl. ................................ 417/477.13; 417/477.2; 604/153
[58] Field of Search ........................ 417/477.2, 477.13; 604/153

[56] References Cited

U.S. PATENT DOCUMENTS

| | | |
|---|---|---|
| 2,406,485 | 8/1946 | Arnold . |
| 3,172,367 | 3/1965 | Kling . |
| 3,591,319 | 7/1971 | Shlisky . |
| 3,784,323 | 1/1974 | Sausse . |
| 4,187,057 | 2/1980 | Xanthopoulos . |
| 4,229,299 | 10/1980 | Savitz et al. . |
| 4,397,639 | 8/1983 | Eschweiler et al. . |
| 4,537,561 | 8/1985 | Xanthopoulos . |
| 4,673,334 | 6/1987 | Allington et al. . |
| 4,735,558 | 4/1988 | Kienholz et al. . |
| 4,767,289 | 8/1988 | Parrott et al. ............................ 417/477 |
| 4,886,431 | 12/1989 | Soderquist et al. . |
| 5,044,902 | 9/1991 | Malbec . |
| 5,082,429 | 1/1992 | Soderquist et al. ...................... 417/477 |
| 5,133,650 | 7/1992 | Sunderland et al. . |
| 5,213,483 | 5/1993 | Flaherty et al. . |
| 5,222,880 | 6/1993 | Montoya et al. . |
| 5,257,917 | 11/1993 | Minarik et al. . |
| 5,433,588 | 7/1995 | Monk et al. . |
| 5,460,490 | 10/1995 | Carr et al. ............................... 417/44.2 |
| 5,486,099 | 1/1996 | Montoya . |
| 5,518,378 | 5/1996 | Neftel et al. . |
| 5,676,530 | 10/1997 | Nazarifar ................................. 417/360 |

OTHER PUBLICATIONS

Linvatec Irrigation Console, Introducing the Easy–To–Use Linvatec Irrigation Console, 1998.

*Primary Examiner*—Timothy S. Thorpe
*Assistant Examiner*—Ehud Gartenberg
*Attorney, Agent, or Firm*—Gene Warzecha

[57] ABSTRACT

A peristaltic pump tubing system for use with a peristaltic pump roller assembly in a surgical procedure. The system comprises a uniquely shaped disposable tubing cassette for retaining the tubing to be used during the surgical procedure and a uniquely shaped cassette holding station situated adjacent the peristaltic pump roller assembly. The cassette comprises a housing containing a flexible tube for engagement with the peristaltic rollers and having an open end to enable the cassette to be moved downwardly to place the tube in alignment with the plane in which the peristaltic rollers rotate. The cassette holding station is provided with a front panel extending in a plane parallel to the roller plane of rotation, the panel being spaced from the pump housing by a sufficient amount to create a pump roller station into which the cassette may fit. The front panel thus holds the cassette tubing in place against the rollers and a single resilient latch at the bottom of the cassette is used to hold the cassette down in place. Simply pulling the tab on the cassette away from the rollers will release the cassette and enable it to be removed from the pump station.

6 Claims, 4 Drawing Sheets

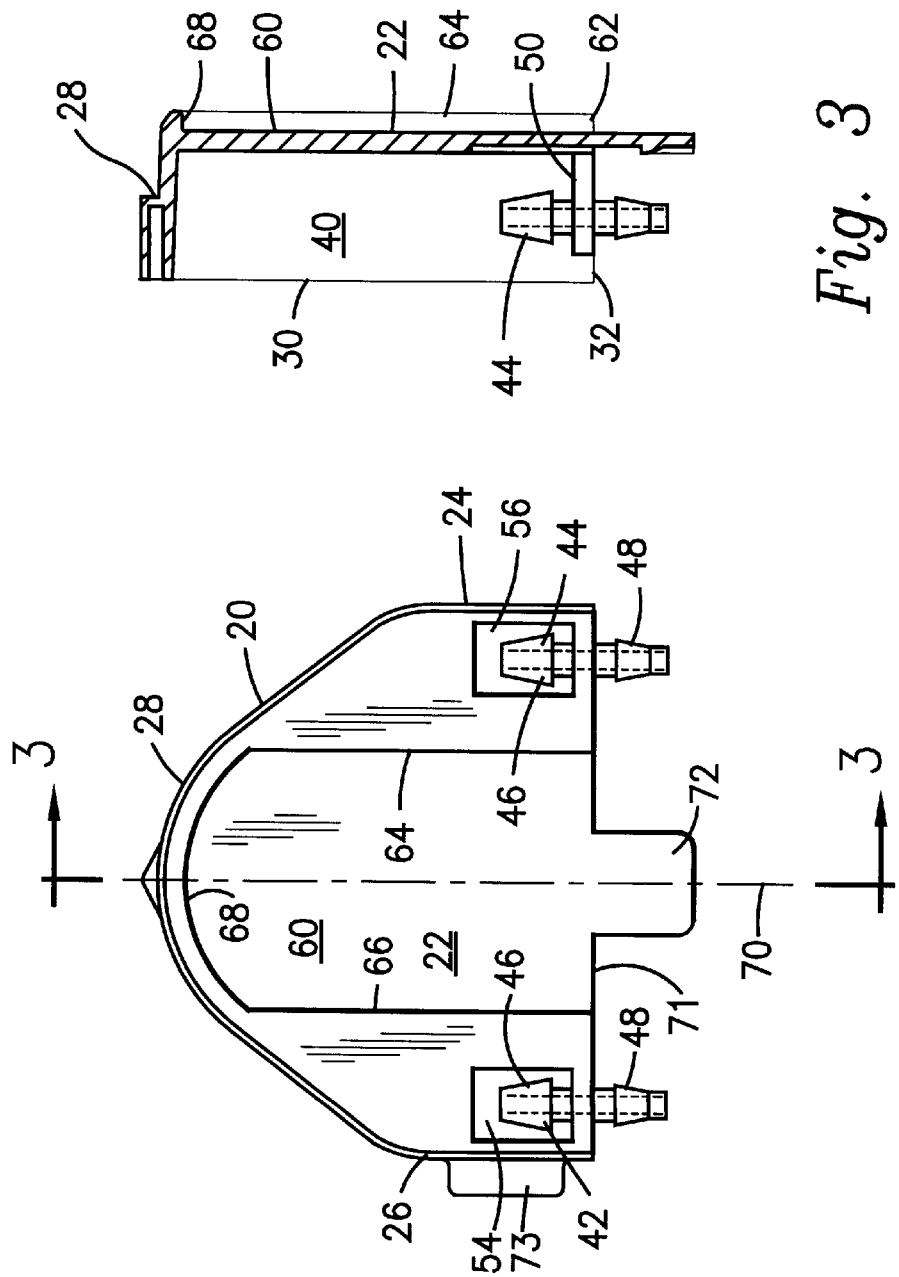

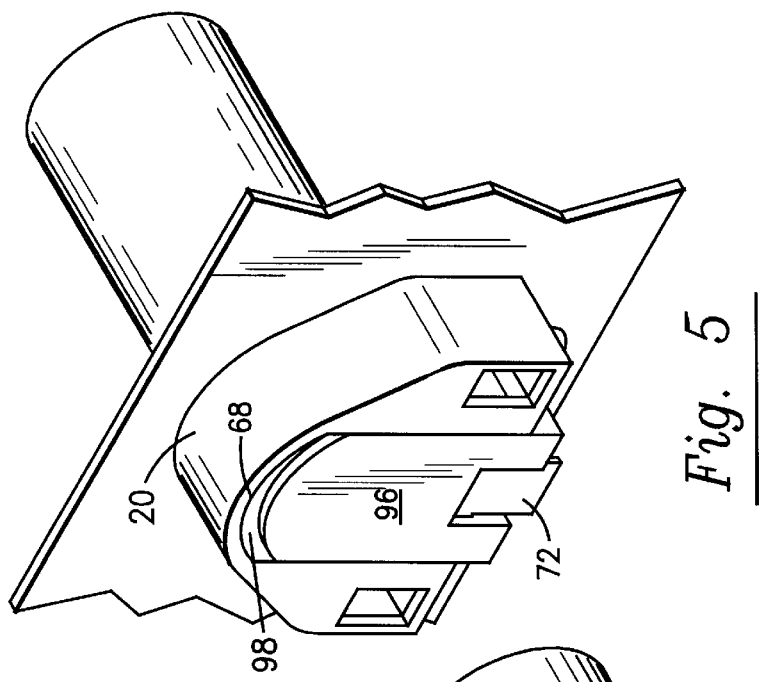
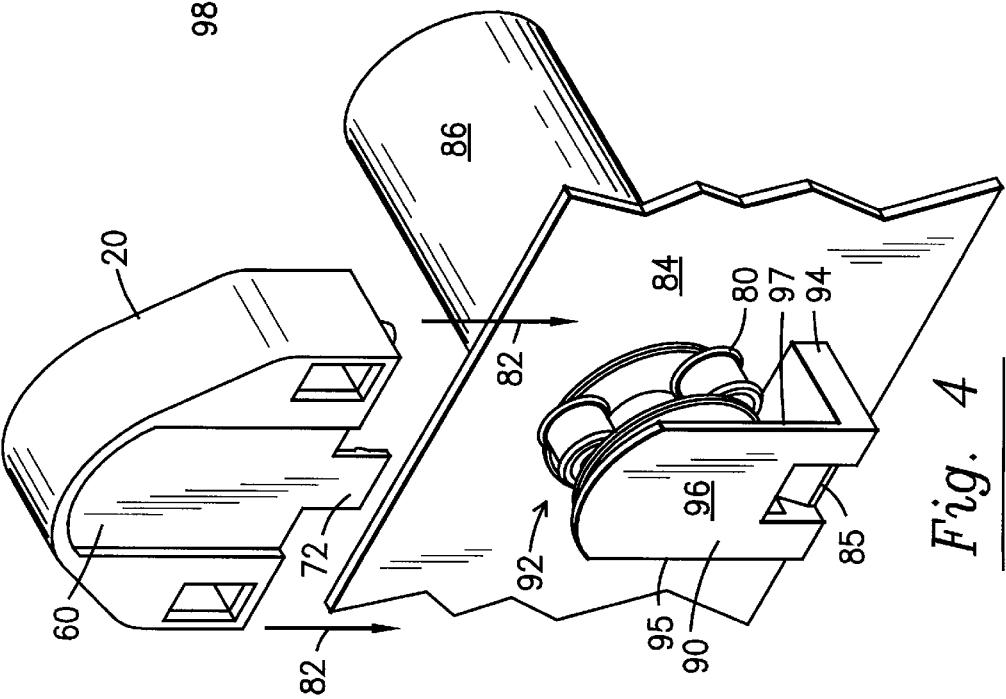

PERISTALTIC PUMP TUBING SYSTEM WITH LATCHING CASSETTE

BACKGROUND OF THE INVENTION

1. Field of the Invention

The invention relates generally to peristaltic pumps and tubing sets for use therewith. More particularly, the invention relates to a tubing cassette which holds a tube adjacent the peristaltic rollers.

2. Description of the Prior Art

Peristaltic pumps are frequently used in medical and surgical applications in order to pump various fluids during surgical procedures. Numerous designs are known by which the tubing used with peristaltic pumps may be relatively easily engaged with the peristaltic pump roller assembly. These designs generally utilize a cassette in the form of a molded housing which retains a portion of the tubing so that the engagement of the tubing with the peristaltic pump simply requires the attachment of the cassette adjacent the peristaltic pump roller assembly rather than the laborious process of threading a tube around the roller assembly and securing it in place.

One type of tubing cassette is shown in U.S. Pat. No. 5,460,490 (Carr et al.) assigned to the assignee hereof and showing a cassette in the form of a molded block having various channels for holding a tube in a predetermined orientation in the plane of rotation of the peristaltic pump roller assembly. The cassette shown in this patent is retained adjacent the roller assembly by a cam device which presses the cassette against the front panel of the peristaltic pump and holds the tube firmly against the roller assembly without a backing plate. The device is relatively complex and requires more manipulation of the cassette than is desired in certain surgical applications.

Another type of "cassette" is shown in U.S. Pat. No. 5,133,650 (Sunderland et al.) in which the tubing is provided with various fixed molded components which are attachable to complementarily shaped recesses in the pump housing and a pivotable swing arm. The latter may then be swung into place in order to stretch the tube about the peristaltic pump roller assembly. This device is really a two-piece device as opposed to a one-piece cassette and is, therefore, not strictly a cassette as that term is normally understood. However, such "cassettes" are representative of available prior art. A similar "cassette" device is used without a swing arm in the Linvatec C7050 Irrigation Console available from Linvatec Corporation, 11311 Concept Boulevard, Largo, Fla. 33773. This device utilizes a peristaltic pump having a pump roller assembly situated adjacent fixed tube-holding stations designed to be used with a tubing set having fixed molded components secured thereto. The tubing set is used by first placing one of the molded components into one of the tube-holding stations adjacent the roller assembly, then stretching the tube around the roller assembly and securing the other molded component in the other tube-holding station. This arrangement holds the tube in generally a U-shape around the peristaltic pump roller assembly as is often done in peristaltic pumps.

Other cassette arrangements are also known in which a one-piece cassette is used with a pair of latching mechanisms in order to hold the tubing cassette in proper position adjacent the peristaltic pump roller assembly. For example, U.S. Pat. No. 5,433,588 (Monk et al) shows a cassette maintained adjacent a peristaltic pump roller assembly by the cooperative action of a pair of spaced locking surfaces, spaced on either side of the rollers. This device operates with a backing plate so that the peristaltic rollers squeeze the tube between the rollers and the backing plate. The device is relatively complex.

Another known disposable cassette for use with a peristaltic pump is shown in U.S. Pat. No. 4,537,561 (Xanthopoulos). The cassette of this device operates without a backing plate and is secured adjacent the pump by a pair of articulating latch arms which hold opposing sides of the cassette adjacent the pump roller assembly station. While this patent makes a reference to a mechanical or electromechanical arrangement utilized to release this locking mechanism, no such arrangement is shown. However, one can reasonably expect it to be relatively complex since the articulating arms must both be moved simultaneously.

It is accordingly an object of this invention to produce a simple, disposable tubing cassette for use with a peristaltic pump roller assembly.

It is another object of this invention to produce a peristaltic pump roller tubing system which enables a tube to be engaged with a peristaltic pump roller assembly in a single manual operation.

It is a further object of this invention to enable such a tubing cassette to be disengaged from the peristaltic pump roller assembly in a simple manual operation.

SUMMARY OF THE INVENTION

These and other objects are accomplished by the preferred embodiment of the system disclosed herein which comprises a peristaltic pump tubing system for use with a peristaltic pump roller assembly. The roller assembly is rotatable in a plane perpendicular to an axis of rotation. While the preferred embodiment is described in terms of a vertical plane of rotation and horizontal axis, it will be understood that any orientation is feasible. The system comprises a flexible tube and a cassette for positioning the tube adjacent the pump roller assembly. The cassette comprises an enclosure containing at least a portion of the flexible tube in a configuration adapted to be placed adjacent to the pump roller assembly. The enclosure is provided with a front surface and a pair of support means at points spaced apart a first predetermined distance and fixed relative to the front surface for holding the flexible tube. The tube is maintained in a U-shaped configuration in a plane and the enclosure has an open bottom end situated between the spaced apart points and in the plane of the flexible tube. A resilient tab extends a second predetermined distance downwardly from the front surface, the resilient tab having a locking edge and a predetermined width less than the spacing between the spaced apart, tube holding points. A cassette holding station is defined adjacent the pump roller assembly, the holding station comprising a support member fixed relative to and below the pump roller assembly and a flat panel aligned in a plane parallel to the plane of rotation of the pump roller assembly and spaced a predetermined distance therefrom. The flat panel extends upwardly a third predetermined distance from the support member and a latch means is provided for engaging the locking edge of the resilient tab to thereby secure the cassette in the cassette holding station. The system operates such that, when the cassette is moved vertically onto the pump roller assembly the flexible tube will engage the pump roller assembly, the front surface will be urged toward the pump roller assembly by the flat panel and the locking edge will engage the latch means to hold the cassette in place.

The invention also resides in the method of attaching a tubing cassette to a peristaltic pump. The method comprises the steps of providing a peristaltic pump roller station having a single latching member as described above. The method further comprises the steps of providing the tubing cassette described above and sliding it into place in the plane of the rollers.

BRIEF DESCRIPTION OF THE DRAWINGS

FIG. 2 is a front elevational view of the tubing cassette of the tubing set shown in FIG. 1.

FIG. 3 is a cross-sectional view of FIG. 2 taken along the line 3—3.

FIG. 4 is a diagrammatic front perspective view of the tubing cassette of FIG. 2 being engaged with a peristaltic pump roller assembly.

FIG. 5 is a view of the components of FIG. 4 shown in assembled configuration.

DESCRIPTION OF THE PREFERRED EMBODIMENT

Figure 1:
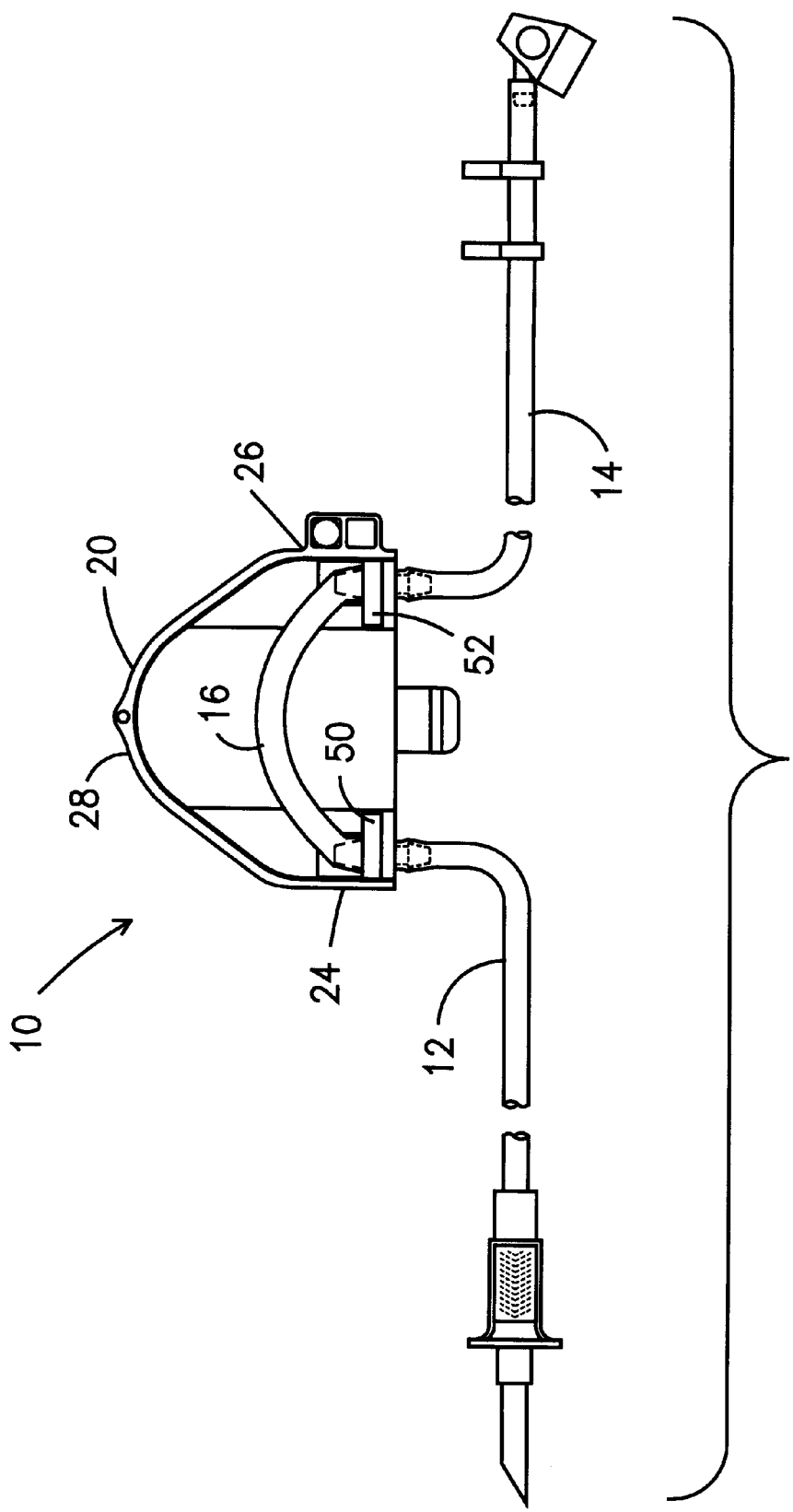
FIG. 1 is a diagrammatic rear elevation view of an exemplary tubing set which may be used with the preferred embodiment of the peristaltic pump tubing system disclosed herein.

Referring now to the drawings there is shown a representative sample of a tubing set 10 which may be used with a peristaltic pump roller assembly. Tubing set 10 comprises an inlet tube assembly 12, an outlet tube assembly 14 and an intermediate tube 16 situated within tubing cassette 20. Inlet tube assembly 12 may be provided with an appropriate connector at its end in order to enable the tube assembly to be connected to a suitable fluid source for use during a particular surgical procedure. The fluid source may be, for example, a conventional bag of saline if the tubing set is to be used to provide irrigation at a surgical site. Similarly, outlet tube assembly may have a variety of connections at its end in order to enable the fluid from the fluid source to be used as intended (e.g. irrigation, motor cooling, etc.). Intermediate tube 16 is, in the preferred embodiment, a separate tube attached at each end to a fitting (as will be explained below). However, it will be understood by those skilled in the art that tube assemblies 12 and 14 and intermediate tube 16 could all be formed as one integral piece.

Tubing cassette 20 comprises an enclosure having a front surface 22, side surfaces 24 and 26, a top surface 28, an open back 30 and an open bottom 32. All of these elements enclose a space 40 within which tube 16 is situated. As best seen in FIGS. 2 and 3, cassette 20 further comprises a pair of spaced cannulated barb assemblies 42 and 44 adapted to receive flexible tube 16 at each end thereof. Each barb assembly has an inward end 46 and an outward end 48, the inward end for being connected to tube 16 and the outward end for being connected to the inlet and outlet tube assemblies 12, 14. The barb assemblies are securely attached at spaced apart points to a spaced pair of ledges 50 and 52 extending inwardly from side surfaces 24 and 26, respectively. The ledges may be attached to the front surface, if desired, and a pair of apertures 54, 56 may be provided in front surface 22 to facilitate molding and/or enhance visibility of the tubing connections.

Front surface 22 is provided with a recessed area 60 having an open bottom side 62 and bounded by linear side shoulders 64 and 66 and an arcuate top shoulder 68. Centrally situated along the axis 70 of cassette 20 is a resilient tab 72 formed as a planar extension of front face 22 and extending beyond the bottom edge 71 thereof. It will be understood that cassette 20 is molded from a suitable plastic or other material having sufficient resiliency to enable tab 72 to be deformed from its normally vertical orientation to engage and disengage a latch as will be described below.

Cassette 20 is also provided with a thin lateral extension 73 which supports on its back surface one or more areas 74 which are intended to carry some indicia (e.g. white or black dot, bar code, etc.). The indicia may be detected by a sensor (not shown) on the pump console to indicate the presence or absence of the cassette in its proper operating position. This prevents inadvertent operation of the pump.

Figure 6:
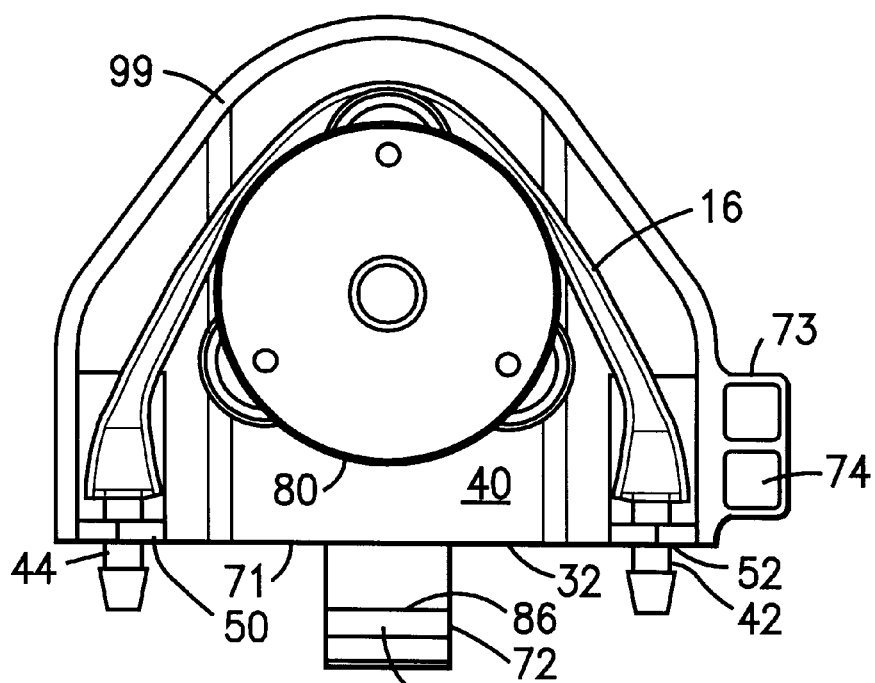
FIG. 6 is a rear elevational view of the cassette and pump roller assembly of FIG. 5.

The method of attachment and use of cassette 20 will be best understood by reference to FIGS. 4–6. As shown in FIG. 4, cassette 20 (shown without the tubes for clarity) is intended to be positioned adjacent a peristaltic pump roller assembly 80 by being moved in the direction of arrows 82 in order to position pump roller assembly 80 within the interior 40 of the cassette 20 as best seen in FIG. 6. While shown in a vertical orientation, it will be understood this is only for reference and the system will be used with the component parts oriented horizontally or otherwise. Pump roller assembly 80 is situated adjacent a surface 84 of a peristaltic pump console or control unit containing motor 186. Pump roller assembly 80 is adapted to be rotated within a plane P perpendicular to axis 88, best seen in FIG. 7, the plane being spaced a predetermined distance in front of and parallel to surface 84 of the control unit.

Pump roller assembly 80 is provided with an adjacent support structure 90 which defines a peristaltic pump roller station 92 between the support structure 90 and surface 84 and adjacent the peristaltic pump roller assembly 80. Support structure 90 comprises a base 94 extending outwardly from surface 84 and an upwardly extending flat front panel 96 extending upwardly from the distal end of support member 94. Front panel 96 is intended to urge the cassette toward the pump roller assembly. The size and shape of front panel 96 is made to fit within recess 60 of cassette 20 as the cassette is moved in direction 82. Panel 96 is bounded by parallel side edges 95 and 97 adapted to engage the side shoulders 64 and 66 of the recess 60 in order to automatically guide the cassette into place and prevent it from twisting during pump operation. Cassette 20 is pushed downwardly into the pump roller station 92 until tube 16 is stretched sufficiently to be closed shut at the 12 o'clock position as shown in FIG. 6. A clearance space 98 may be left between the top edge of front panel 96 and the arcuate shoulder 68 of recess 60. The dimensions of the components of cassette 20 and support chamber 90 are chosen so that when the cassette is properly mounted, tube 16 will be properly stretched and bottom edge 71 will rest on or be slightly (e.g. 1 mm) above the top surface of support member 94 while the back edge 99 of the top and side surfaces (24, 26, 28) will touch or be slightly spaced from surface 84.

Figure 7:
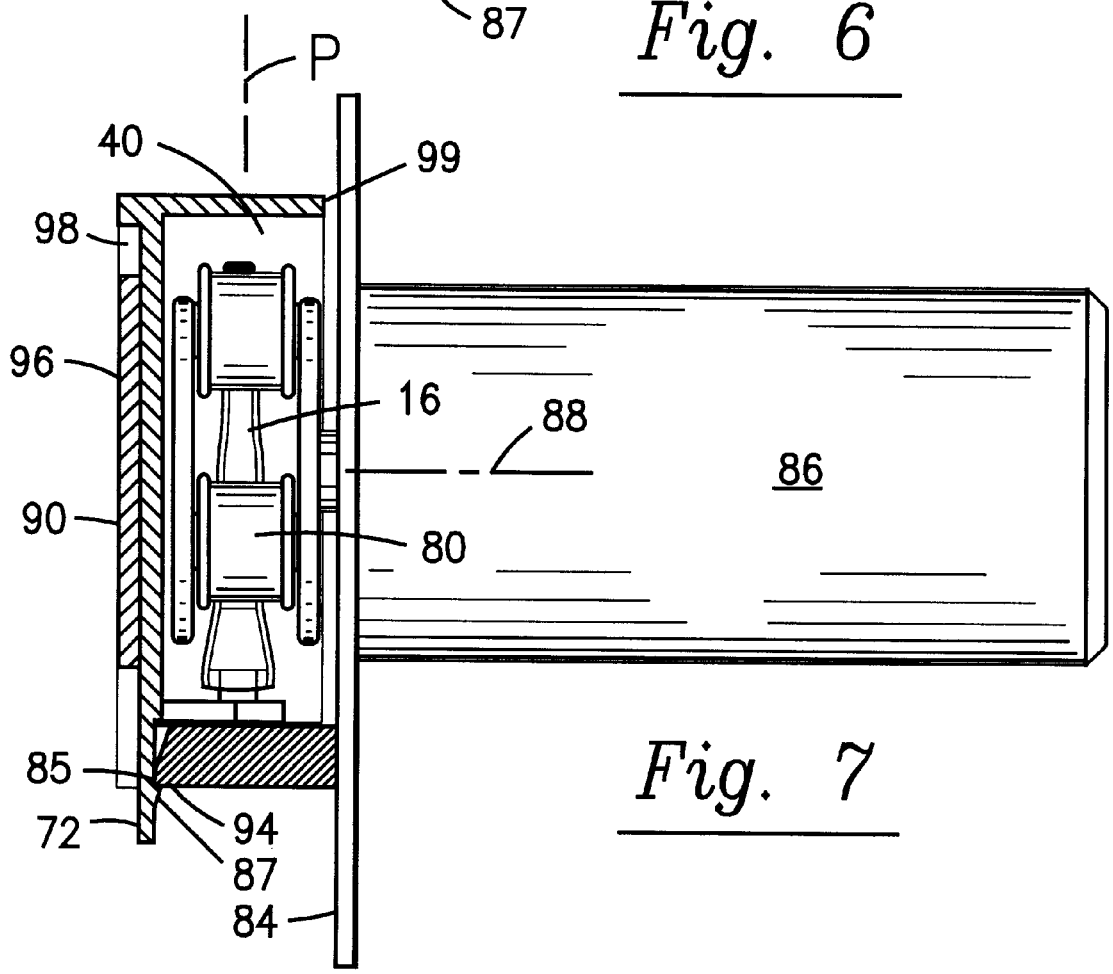
FIG. 7 is a side elevational view in cross-section of FIG. 5.

The bottom portion of front panel 96 is cut away to provide clearance for tab 72 and to provide access to the front edge 85 of support member 94 which acts as a latching mechanism for edge 86 of tab 72 as best seen in FIG. 7. The tab 72 is sufficiently resilient to enable it to be deformed away from support member 94 as ramp 87 slides on edge 85 to enable edges 85 and 86 to engage and thereby lock the cassette into place. When the surgical procedure is completed, the tubing set may be removed from the pump console by simply pulling tab 72 outwardly to disengage edges 85 and 86 and allow the resilience of the stretched tube 16 to "eject" the cassette from the pump roller station 92. Because of the simple design of the system, both attachment and detachment of the cassette are single-handed operations.

While tube 16 is shown being held in a U-shaped configuration to facilitate the engagement of the tube with the pump roller assembly, those skilled in the art will understand that the invention may be adapted to a cassette in which tube 16 could be straight or otherwise depending on the intended manner of use.

It will be understood by those skilled in the art that numerous improvements and modifications may be made to the preferred embodiment of the invention disclosed herein without departing from the spirit and scope thereof.

What is claimed is:

1. A peristaltic pump tubing system for use with a peristaltic pump roller assembly rotatable in a vertical plane perpendicular to an axis comprising:

a flexible tube;

a cassette for positioning said flexible tube adjacent said pump roller assembly, said cassette comprising:

an enclosure containing at least a portion of said flexible tube in a configuration adapted to be placed adjacent to said pump roller assembly for use therewith, said enclosure comprising a front surface, a pair of support means at points spaced apart a first predetermined distance and fixed relative to said front surface for holding said flexible tube in said configuration, and an open bottom end situated between said spaced apart points;

a resilient tab extending a second predetermined distance downwardly from said front surface, said resilient tab having a locking edge and a predetermined width less than said first predetermined distance;

a cassette holding station adjacent said pump roller assembly, said holding station comprising:

a support member fixed relative to and below said pump roller assembly;

a flat panel aligned in a plane parallel to said plane of rotation of said pump roller assembly and spaced a predetermined distance therefrom, said flat panel extending upwardly a third predetermined distance from said support member;

a latch means for engaging said locking edge of said resilient tab to thereby secure said cassette in said cassette holding station;

whereby, when said cassette is moved vertically onto said pump roller assembly said flexible tube will engage said pump roller assembly, said front surface will be urged toward said pump roller assembly by said flat panel and said locking edge will engage said latch means.

2. A peristaltic pump tubing system according to claim 1 further comprising side and top surfaces attached and extending perpendicularly to said front surface to thereby partially enclose said flexible tube.

3. A peristaltic pump tubing system according to claim 1 further comprising:

a pair of vertical side edges bounding said flat panel;

a pair of spaced shoulders bounding said recess for engaging said side edges; and a recess on said front surface for receiving said flat panel.

4. A method for attaching a tubing cassette to hold tubing adjacent a plurality of peristaltic pump rollers rotating about an axis perpendicular to a front panel comprising the steps of:

providing a pump roller station adjacent said rollers, said pump roller station comprising a support panel having a predetermined width and extending upwardly in a plane parallel to and spaced from said rollers and defining a pump roller station between said support panel and said front panel;

providing a single latching member along the vertical centerline of said support panel at a position adjacent the bottom thereof;

providing a tubing cassette for holding said tubing in a U-shaped orientation, said tubing cassette comprising a housing having a predetermined depth to enable it to fit within said pump roller station between said support panel and said front panel and a single resilient tab adapted to engage said single latching member when said tubing cassette is moved downwardly a predetermined distance into said pump roller station; and sliding said tubing cassette into said pump roller station to place said housing adjacent said support panel and engage said tab member with said latching member.

5. A method according to claim 4 wherein said tab member has an extension extending beyond said latching member further comprising the step of releasing said cassette from said tubing station by manually bending said extension so as to disengage said tab member and said latching member.

6. A method according to claim 4 wherein said support panel and said housing are each provided with at least one complementarily shaped vertically extending projection in order to enable said tubing cassette to be automatically aligned with said support panel to properly engage said tab member and said latching member.

* * * * *